(12) United States Patent
Lee et al.

(10) Patent No.: US 9,238,225 B2
(45) Date of Patent: Jan. 19, 2016

(54) FLUID CONTROLLING APPARATUS AND METHOD OF CONTROLLING FLUID BY USING THE SAME

(75) Inventors: June-young Lee, Anyang-si (KR); Sang-hyun Baek, Hwaseong-si (KR); Hyo-young Jeong, Incheon (KR); Tae-seok Sim, Seoul (KR); Jeong-gun Lee, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 556 days.

(21) Appl. No.: 13/571,202

(22) Filed: Aug. 9, 2012

(65) Prior Publication Data

US 2013/0086998 A1  Apr. 11, 2013

(30) Foreign Application Priority Data

Oct. 5, 2011  (KR) ........................ 10-2011-0101412

(51) Int. Cl.
*G01N 1/20* (2006.01)
*B01L 3/00* (2006.01)
*G01N 35/00* (2006.01)
*G01N 35/04* (2006.01)

(52) U.S. Cl.
CPC ......... *B01L 3/502753* (2013.01); *B01L 3/5027* (2013.01); *B01L 2200/0621* (2013.01); *B01L 2200/141* (2013.01); *B01L 2300/0681* (2013.01); *B01L 2300/087* (2013.01); *B01L 2300/0861* (2013.01); *B01L 2300/0867* (2013.01); *B01L 2400/0487* (2013.01); *G01N 2035/00237* (2013.01); *G01N 2035/0437* (2013.01); *Y10T 137/4259* (2015.04)

(58) Field of Classification Search
CPC ............ B01L 3/502753; B01L 3/5027; B01L 2200/0621; B08B 3/04; B08B 9/027; Y10T 137/4259
USPC ............................ 137/237, 240, 15.01, 15.04
See application file for complete search history.

(56) References Cited

U.S. PATENT DOCUMENTS

| | | | | |
|---|---|---|---|---|
| 5,375,622 A | * | 12/1994 | Houston | 137/240 |
| 5,944,043 A | * | 8/1999 | Glick et al. | 137/240 |
| 6,387,277 B1 | | 5/2002 | North, Jr. | |
| 2010/0256350 A1 | * | 10/2010 | Rhee et al. | 536/25.4 |

FOREIGN PATENT DOCUMENTS

| | | |
|---|---|---|
| JP | 2005-193152 A | 7/2005 |
| JP | 2007-20729 A | 2/2007 |
| JP | 2007-61611 A | 3/2007 |
| JP | 2010-36079 A | 2/2010 |
| KR | 1020130000968 A | 1/2013 |

* cited by examiner

*Primary Examiner* — Kevin Lee
(74) *Attorney, Agent, or Firm* — Leydig, Voit & Mayer, Ltd.

(57) ABSTRACT

A fluid controlling apparatus including at least one sample chamber for holding a fluid containing target materials; a cleaning chamber for holding a cleaning solution; a first multi-port connected to the at least one sample chamber through a first channel and connected to the cleaning chamber through a second channel; a filter portion, connected to the first multi-port through a third channel, for filtering the target materials; and a first pump, connected to the filter portion, for applying a pressure; and a method of controlling a fluid using the fluid controlling apparatus, which comprises passing the fluid containing the target materials from the at least one sample chamber to the filter portion; and cleaning a path of the fluid by passing the cleaning solution through the path.

20 Claims, 11 Drawing Sheets

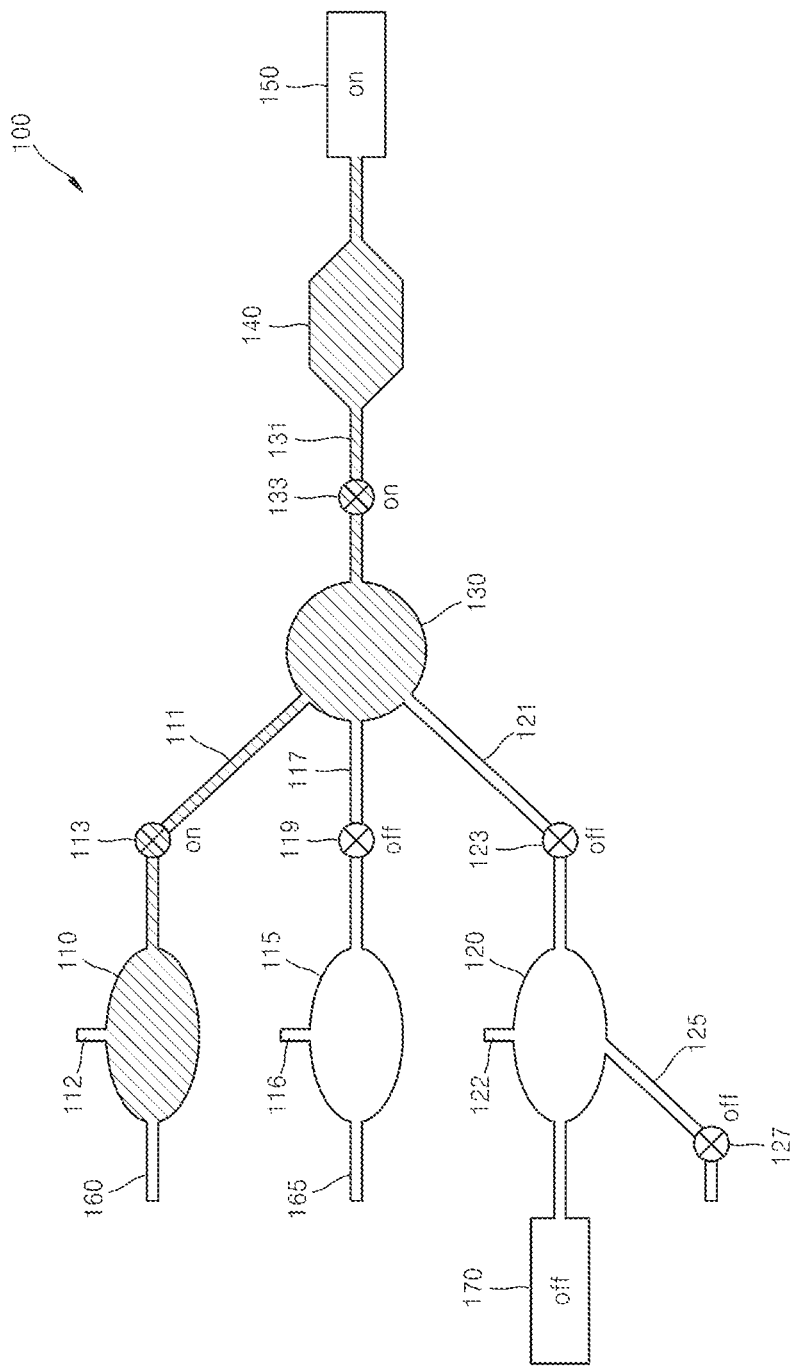

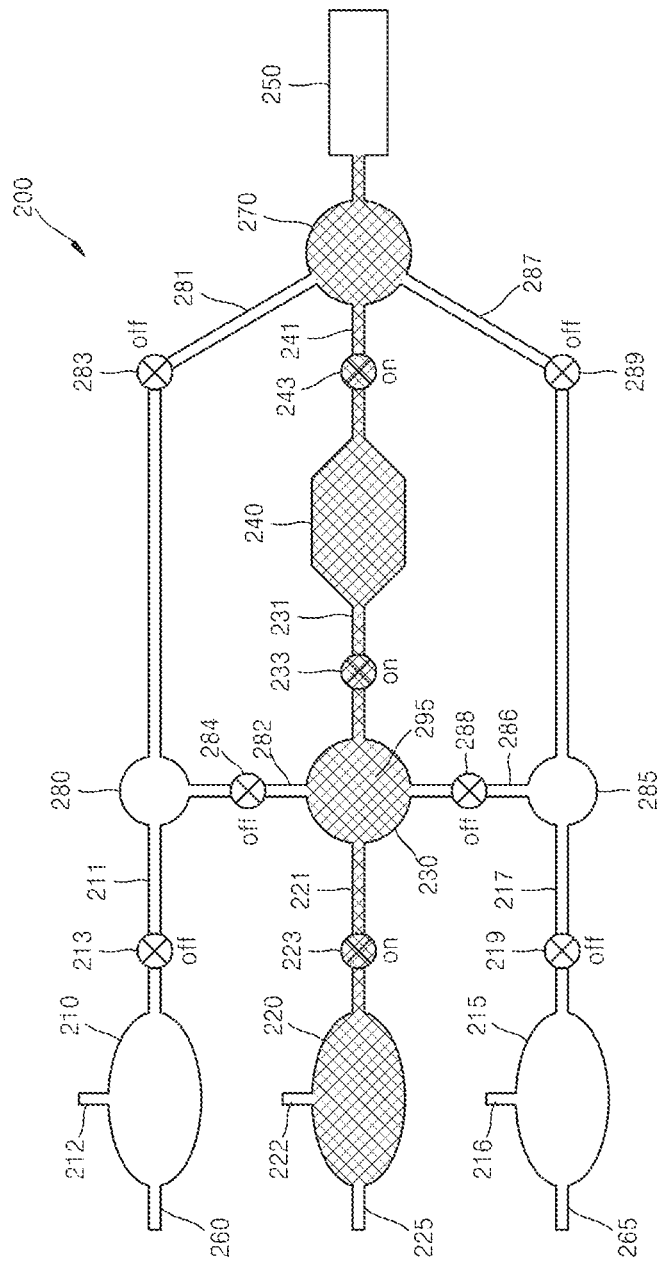

FLUID CONTROLLING APPARATUS AND METHOD OF CONTROLLING FLUID BY USING THE SAME

CROSS-REFERENCE TO RELATED APPLICATIONS

This application claims the benefit of Korean Patent Application No. 10-2011-0101412, filed on Oct. 5, 2011, in the Korean Intellectual Property Office, the disclosure of which is incorporated herein in its entirety by reference.

BACKGROUND

Microfluidic devices are used to perform biological or chemical reactions by manipulating a small amount of fluid. Microfluidic devices may include microfluidic structures arranged within a platform having various shapes such as a chip and a disc. A microfluidic structure may include a chamber which stores a fluid, a channel through which the fluid flows, and a valve which controls fluid flow. The chamber, the channel, and the valve may be disposed in various combinations within a platform. A hydraulic filter is a system for capturing a target material by using a flow of fluids due to a microfluidic structure. A biochip is formed by arranging such microfluidic structures on a chip-type platform so as to perform various assays, including biological reactions, on a small chip.

SUMMARY

Additional aspects will be set forth in part in the description which follows and, in part, will be apparent from the description, or may be learned by practice of the presented embodiments.

According to an aspect of the present invention, a fluid controlling apparatus including at least one sample chamber to which a fluid containing target materials is introduced; a cleaning chamber to which a cleaning solution is introduced; a first multi-port connected to the at least one sample chamber through a first channel and connected to the cleaning chamber through a second channel; a filter portion connected to the first multi-port through a third channel and filtering the target materials; and a first pump connected to the filter portion and applying a pressure.

The first through third channels may further include first through third valves for respectively opening and closing the first through third channels.

The at least one sample chamber and the cleaning chamber may include air vents that are respectively formed therein.

The fluid controlling apparatus may further include a fourth valve for opening and closing the air vent connected to the cleaning chamber; and a second pump connected to the washing chamber and applying a pressure.

The fluid controlling apparatus may further include a second multi-port connected to the filter portion and the first pump.

The fluid controlling apparatus may further include at least one 3-way port for connecting the at least one sample chamber and the first and second multi-ports.

The filter portion may include a plurality of filter sequences including a plurality of filter units.

Each of the plurality of filter units may include a first portion including a plurality of protrusions protruding in a first direction; a second portion that is spaced apart from the first portion to face the first portion and includes a plurality of protrusions that protrude towards the first direction and correspond to the plurality of protrusions of the first portion.

Each of the plurality of filter units may further include a third portion disposed between the first portion and the second portion, a first fluid discharge channel may be formed between the first portion and third portion, and a second fluid discharge channel may be formed between the second portion and the third portion.

According to an aspect of the present invention, a method of controlling a fluid by using the fluid controlling apparatus, the method including passing the fluid containing the target materials from the at least one sample chamber to the filter portion; and cleaning the path through the fluid passes by passing the cleaning solution through the path.

The passing the fluid to the filter portion may include passing the fluid introduced to the at least one sample chamber from the at least one sample to the filter portion through the first multi-port by a pressure applied by the first pump.

The passing the fluid to the filter portion may be performed by opening first and third valves for opening the first and third channels and closing a second valve for opening and closing the second channel.

The cleaning of the path may include cleaning a first path from the cleaning chamber to the at least one sample chamber through the first multi-port; and cleaning a second path from the cleaning chamber to the filter portion through the first multi-port.

The cleaning of the first path may be performed by opening first and second valves for opening the first and second channels, closing a third valve for opening and closing the third channel, closing a fourth valve for opening and closing an air vent included in the cleaning chamber, and applying a pressure to the cleaning chamber.

The first pump may not be driven, and a second pump connected to the cleaning chamber may apply the pressure to the cleaning chamber.

The cleaning of the second path may be performed by closing a first valve for opening and closing the first channel, and opening second and third valves for opening and closing the second and third channels.

The first pump may apply the pressure to the fluid controlling apparatus, and a second pump connected to the cleaning chamber may not be driven.

The fluid controlling apparatus may include a second multi-port connected to the filter portion and the first pump; and at least one 3-way port for connecting the at least one sample chamber and the first and second multi-ports, the passing of the fluid to the filter portion may include passing the fluid introduced to the at least one sample chamber from the at least one sample chamber to the filter portion and the second multi-port through the at least one 3-way port and the first multi-port by the pressure applied by the first pump.

The passing the fluid to the filter portion may be performed by closing a second valve for opening and closing the second channel, and closing a fifth valve for opening and closing a fifth channel connecting the at least one 3-way port and the second multi-port.

The cleaning of the path may include cleaning a third path from the cleaning chamber to the second multi-port through the first multi-port and the at least one 3-way port; and cleaning a fourth path from the cleaning chamber to the filter portion and the second multi-port through the cleaning chamber and the first multi-port.

The cleaning of the third path may be performed by closing first and third valves for respectively opening and closing the first and third channels.

The cleaning of the fourth path may be performed by closing a fifth valve for opening and closing a fifth channel for connecting the at least one 3-way port and the second multi-port, and closing a sixth valve for closing and opening a sixth channel for connecting the at least one 3-way port and the first multi-port.

BRIEF DESCRIPTION OF THE DRAWINGS

These and/or other aspects will become apparent and more readily appreciated from the following description of the embodiments, taken in conjunction with the accompanying drawings in which:

FIG. 2 is a structural diagram for describing a method of controlling a fluid by using a fluid controlling apparatus, according to an embodiment of the present invention;

FIGS. 7A and 7B are structural diagrams for describing a method of controlling a fluid by using a fluid controlling apparatus, according to another embodiment of the present invention.

DETAILED DESCRIPTION

Figure 1:
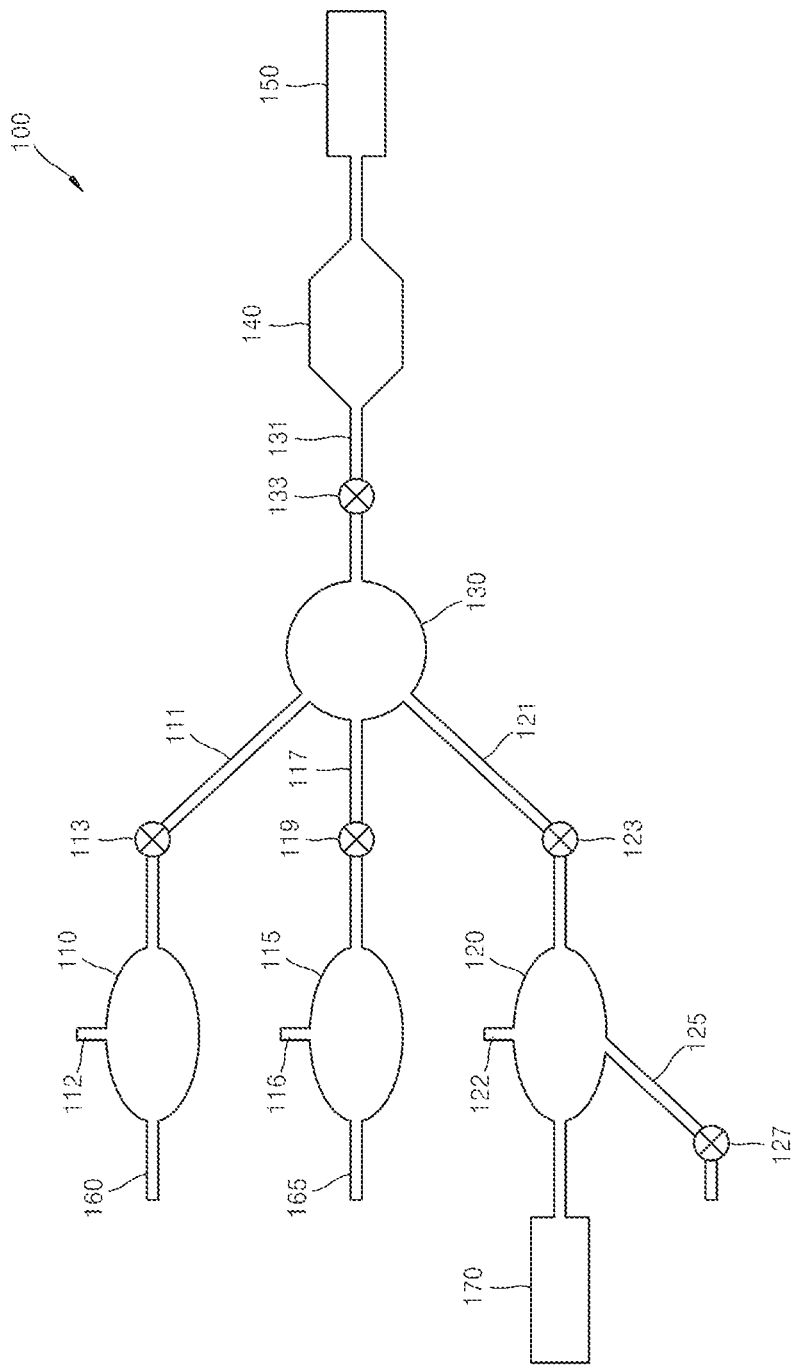
FIG. 1 is a schematic structural diagram of a fluid controlling apparatus according to an embodiment of the present invention.

Various example embodiments will now be described more fully with reference to the accompanying drawings in which some example embodiments are shown.

Detailed illustrative example embodiments are disclosed herein. However, specific structural and functional details disclosed herein are merely representative for purposes of describing example embodiments. This invention may, however, may be embodied in many alternate forms and should not be construed as limited to only the example embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items.

It will be understood that when an element or layer is referred to as being "formed on," another element or layer, it can be directly or indirectly formed on the other element or layer. That is, for example, intervening elements or layers may be present. In contrast, when an element or layer is referred to as being "directly formed on," to another element, there are no intervening elements or layers present. Other words used to describe the relationship between elements or layers should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

In the drawings, the thicknesses of layers and regions are exaggerated for clarity. Like reference numerals in the drawings denote like elements.

Hereinafter, an apparatus for controlling fluid and a method of controlling fluid by using the same will be described with regard to exemplary embodiments of the invention with reference to the attached drawings.

FIG. 1 is a schematic structural diagram of a fluid controlling apparatus 100 according to an embodiment of the present invention.

Referring to FIG. 1, the fluid controlling apparatus 100 may include at least one sample chamber, a cleaning chamber 120, a first multi-port 130 that is connected to the at least one sample chamber and the cleaning chamber 120, a filter portion 140 that is connected to the first multi-port 130 and filters target materials, and a first pump 150 connected to the filter portion 140.

The at least one sample chamber may include first and second sample chambers 110 and 115. A fluid including the target materials may be introduced to each of the first and second sample chambers 110 and 115. The fluid may be introduced to the first and second sample chambers 110 and 115 through first and second inlets 112 and 116 that are included in the first and second sample chambers 110 and 115, respectively, from outside the fluid controlling apparatus 100. FIG. 1 shows a case where two sample chambers, that is, the first and second sample chambers 110 and 115, are used. However, the number of sample chambers may differ.

A cleaning solution may be introduced to the cleaning chamber 120 and may clean components of the fluid controlling apparatus 100. For example, the cleaning solution may remove pollutants that remain on channels, sample chambers, or the like of the fluid controlling apparatus 100. The cleaning solution may be introduced to the cleaning chamber 120 through a third inlet 122 included in the cleaning chamber 120. FIG. 1 shows a case where a single cleaning chamber, that is, the cleaning chamber 120 is used. However, the number of cleaning chambers may differ.

The first multi-port 130 may be connected to the first and second sample chambers 110 and 115 through first and second channels 111 and 117, respectively. The first multi-port 130 may be connected to the cleaning chamber 120 through a third channel 121. The first through third channels 111, 117, and 121 may include first through third valves 113, 119, and 123 for opening and closing respective channels, respectively. That is, the first through third valves 113, 119, and 123 may control flow of fluids that flow through the first through third channels 111, 117, and 121, respectively. For example, when the first valve 113 included in the first channel 111 is turned on, the fluid or the cleaning solution may flow between the first sample chamber 110 and the first multi-port 130 through the first channel 111. On the other hand, for example, when the third valve 123 included in the third channel 121 is turned off, the fluid and the cleaning solution may not flow between the cleaning chamber 120 and the first multi-port 130 through the third channel 121. If the fluid controlling apparatus 100 further includes another sample chamber or another cleaning chamber, more channels may be connected to the first multi-port 130.

The filter portion 140 may filter the target materials included in the fluid. The target materials captured by the filter portion 140 may include various cells or biological molecules. Examples of the cells may include cancer cells, red blood cells (RBCs), white blood cells (WBCs), phagocytes, animal cells, and plant cells. In addition, the biological molecules may include various biomolecules constituting a living organism, such as proteins, lipids, and nucleic acid, for example, deoxyribonucleic acid (DNA) and ribonucleic acid (RNA), but the present embodiment is not limited thereto. The biological molecules may include aptamers, antigens, antibodies, enzymes, enzyme substrates, enzyme inhibitors, receptors, receptor ligands, or the like. If target materials are biological molecules, since the sizes of the biological molecules range from several nanometer (nm) to several hundred nm, the size of a filter unit (not shown) included in the filter portion 140, that is, the size of a capturing portion of the filter unit, may range from several nm to several hundred nm.

For example, the target materials may include circulating tumor cells (CTCs) included in blood. The number of CTCs may be so small that only one CTC is detected from among about $10^9$ cells. For example, in the case of breast cancer, about 5 CTCs or less may be detected in about 7.5 milliliters (ml) of blood, and in the case of colon cancer, 3 CTCs or less may be detected in about 7.5 ml of blood. Accordingly, there is a need to capture a small number of CTCs without loss. Also, since CTCs are easily destroyed, external environmental factors that may destroy CTCs need to be minimized. RBCs, WBCs, blood plasmas, and blood platelets that are included in blood may act as pollutants that contaminate the fluid controlling apparatus 100. The pollutants may remain on channels, valves, ports, sample channels, and the like of the fluid controlling apparatus 100 and may coagulate. Pollutant coagulation may cause a portion of the fluid controlling apparatus 100 to clog. When the target materials are filtered, the pollutants may serve as noise.

The filter portion 140 may include a plurality of filter units that will be described later. The filter portion 140 may be connected to the first multi-port 130 through a fourth channel 131. In addition, the fourth channel 131 may further include a fourth valve 133 that opens and closes the fourth channel 131 and controls a flow of fluid passing through the fourth channel 131.

The first pump 150 may be connected to the filter portion 140. The first pump 150 applies a pressure to the fluid controlling apparatus 100. The fluid including the target materials and the cleaning solution may flow in the fluid controlling apparatus 100. The first pump 150 may apply a negative pressure to the fluid controlling apparatus 100. For example, the first pump 150 may be a vacuum pump. In this case, first through third air vents 160, 165, and 125 may be formed in the first and second sample chambers 110 and 115, and the cleaning chamber 120, respectively. Thus, when the first pump 150 applies a negative pressure to the fluid controlling apparatus 100, air may be introduced from the first through third air vents 160, 165, and 125, and the fluid and the cleaning solution may flow in a direction from the first and second sample chambers 110 and 115 and the cleaning chamber 120 toward the first pump 150. The third air vent 125 included in the cleaning chamber 120 may include a valve 127 for opening and closing the third air vent 125.

A second pump 170 may be connected to the cleaning chamber 120. When the second pump 170 applies a pressure to the cleaning chamber 120, the cleaning solution may flow from the cleaning chamber 120 to the first and second sample chambers 110 and 115 through the first multi-port 130. The second pump 170 may apply a positive pressure to the fluid controlling apparatus 100 and may be, for example, a pressure pump. When the second pump 170 applies a pressure to the fluid controlling apparatus 100, the valve 127 for opening and closing the third air vent 125 may be turned off, that is, may be closed. When the second pump 170 applies a positive pressure to the fluid controlling apparatus 100, the cleaning solution may flow from the cleaning chamber 120 to the filter portion 140 through the first multi-port 130.

A method of controlling a fluid by using the fluid controlling apparatus 100 of FIG. 1 will now be described. The method may include passing the fluid including the target materials from the at least one sample chamber to the filter portion 140 and cleaning a path through which the fluid passes by flowing the cleaning solution through the path.

FIG. 2 is a structural diagram for describing an operation of passing the fluid including the target materials from the at least one sample chamber to the filter portion 140 in the method of controlling a fluid, according to an embodiment of the present invention.

Referring to FIG. 2, the fluid including the target materials may be introduced to the first sample chamber 110 through the first inlet 112. The fluid may flow in a direction from the first sample chamber 110 toward the first pump 150 by a negative pressure applied by the first pump 150. That is, the fluid may flow from the first sample chamber 110 to the first multi-port 130 through the first channel 111. In this case, the first valve 113 for opening and closing the first channel 111 may be turned on, that is, may be opened. The fluid may reach the filter portion 140 through the first multi-port 130 and the fourth channel 131. In this case, the fourth valve 133 for opening and closing the fourth channel 131 may be turned on, that is, may be opened. While the fluid passes through the filter portion 140, the target materials may be filtered and the remaining fluid may be discharged out of the fluid controlling apparatus 100. In the operation of passing the fluid through the filter portion 140, the second valve 119 included in the second channel 117 and the third valve 123 included in the third channel 121 may be turned off, that is, may be closed. In addition, the valve 127 included in the third air vent 125 may also be turned off, that is, may be closed.

Figure 3A:
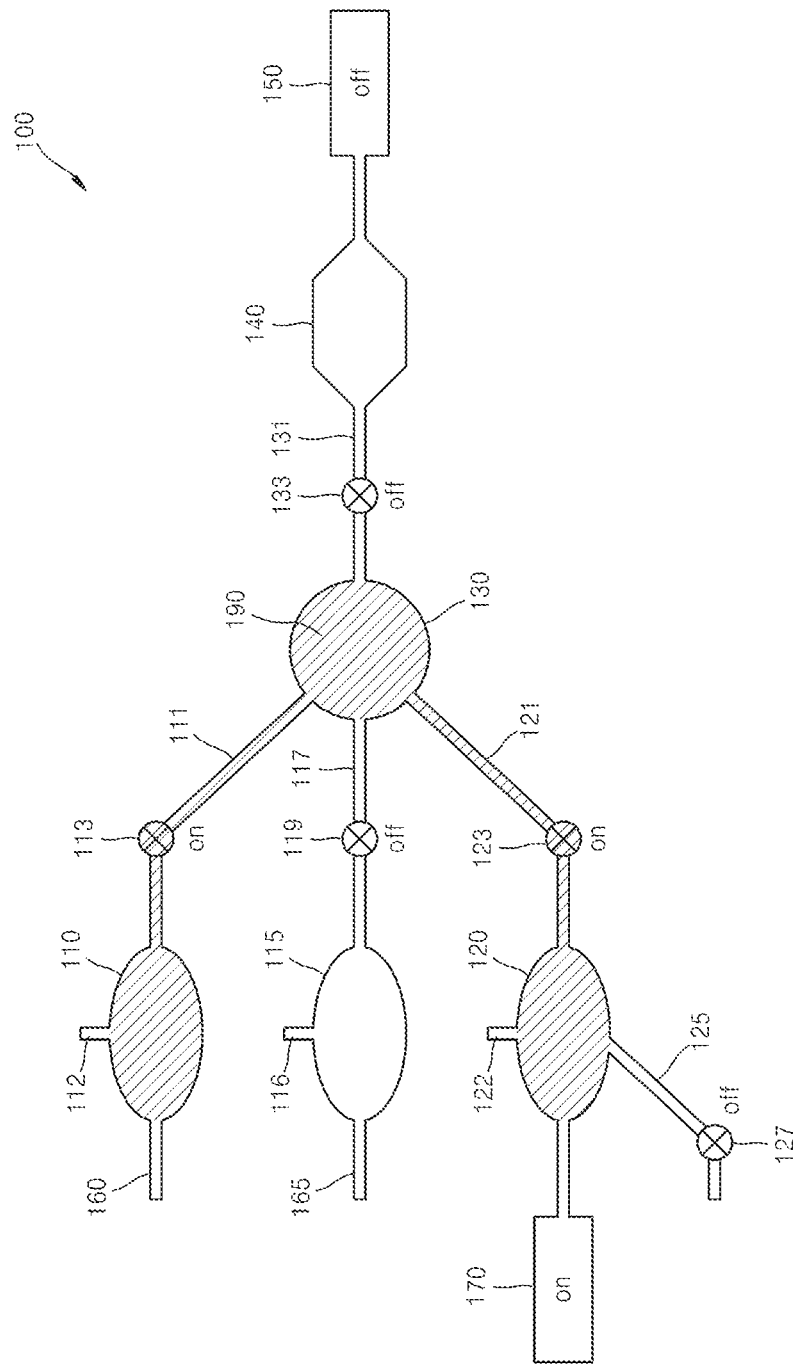
FIGS. 3A and 3B are structural diagrams for describing a method of controlling a fluid by using a fluid controlling apparatus, according to an embodiment of the present invention.
Figure 3B:
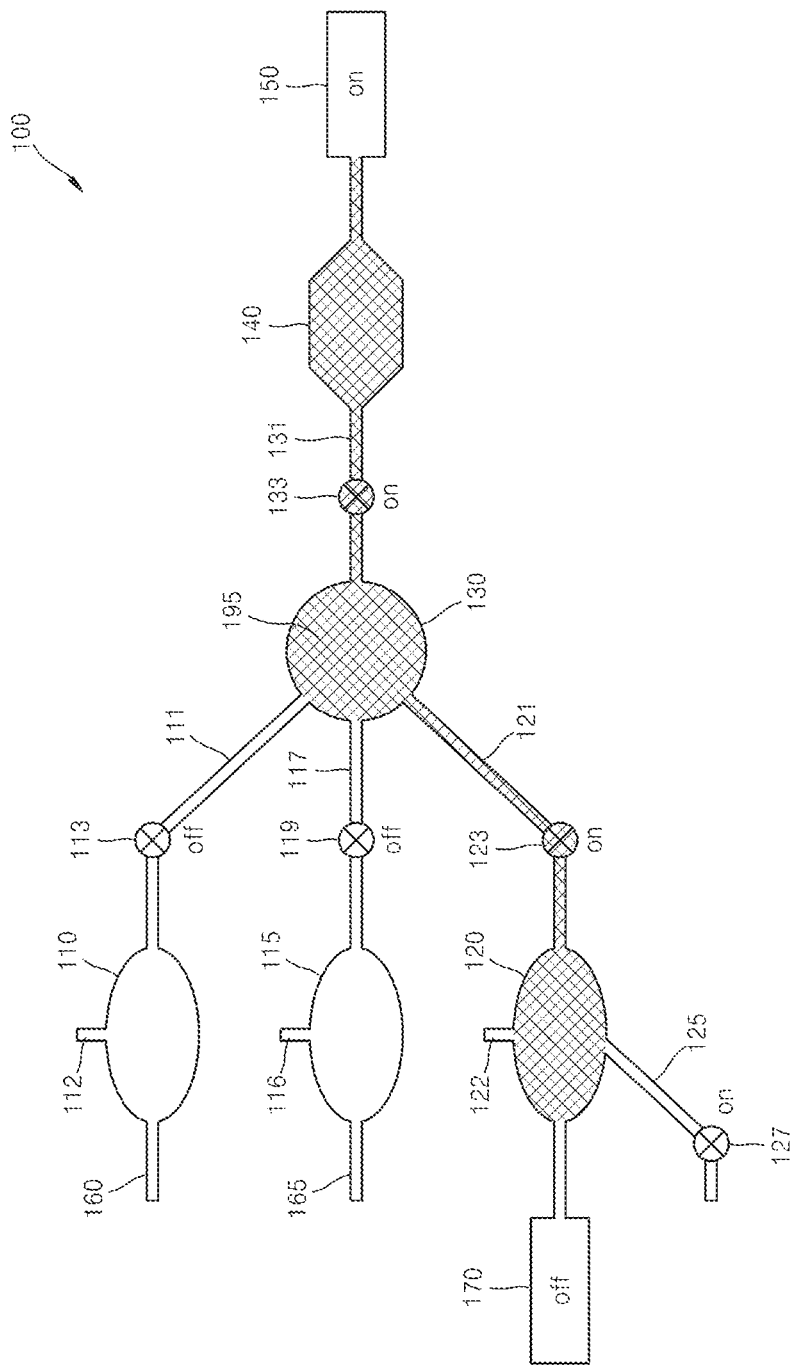

FIGS. 3A and 3B are structural diagrams for describing operations of cleaning paths through which fluids pass in the method of controlling a fluid, according to an embodiment of the present invention.

FIG. 3A shows an operation of cleaning a first path 190. The cleaning solution may be introduced to the cleaning chamber 120 through the third inlet 122. The cleaning solution may flow in a direction from the cleaning chamber 120 toward the first sample chamber 110 by a positive pressure applied by the second pump 170.

In detail, the cleaning solution may flow from the cleaning chamber 120 to the first multi-port 130 through the third channel 121. In this case, since the third valve 123 for opening and closing the third channel 121 may be turned on, that is, may be opened, and the first pump 150 may be turned off, no pressure may be applied to the fluid controlling apparatus 100. The cleaning solution may reach the first sample chamber 110 through the first multi-port 130 and the first channel 111. In this case, the first valve 113 for opening and closing the first channel 111 may be turned on, that is, may be opened. The cleaning solution may remove the fluid and pollutants or the like included in the fluid, which remain on the first path 190 while passing through the first path 190. Thus, the fluid controlling apparatus 100 may prevent components of the fluid controlling apparatus 100 from being contaminated by the pollutants and the path through which the fluid passes from clogging due to the pollutants. The cleaning solution may be discharged out of the fluid controlling apparatus 100 through an outlet (not shown) included in the first sample chamber 110.

In the operation of cleaning the first path 190, the second valve 119 included in the second channel 117 and the fourth valve 133 included in the fourth channel 131 may be turned off, that is, may be closed. The valve 127 for opening and closing the third air vent 125 included in the cleaning chamber 120 may also be turned off, that is, may be closed.

FIG. 3B shows an operation of cleaning a second path 195. The cleaning solution may be introduced to the cleaning chamber 120 through the third inlet 122. The cleaning solution may flow in a direction from the cleaning chamber 120 toward the first pump 150 by a negative pressure applied by the first pump 150.

In detail, the cleaning solution may flow from the cleaning chamber 120 to the first multi-port 130 through the third channel 121. In this case, the third valve 123 for opening and closing the third channel 121 may be turned on, that is, may be opened, and the second pump 170 may be turned off, that is, no pressure may be applied to the fluid controlling apparatus 100. In addition, the valve 127 included in the third air vent 125 may be turned on, that is, may be opened, and thus the cleaning solution may flow from the cleaning chamber 120 through the second path 195 by a negative pressure. The cleaning solution may reach the filter portion 140 through the first multi-port 130 and the fourth channel 131. In this case, the fourth valve 133 for opening and closing the fourth channel 131 may be turned on, that is, may be opened. The cleaning solution may remove the fluid and pollutants or the like included in the fluid, which remain on the second path 195 while passing through the second path 195. Thus, the fluid controlling apparatus 100 may prevent components of the fluid controlling apparatus 100 from being contaminated by the pollutants and the path through which the fluid passes from clogging due to the pollutants. The cleaning solution may clean the filter portion 140 and may be discharged out of the fluid controlling apparatus 100 through an outlet (not shown). In the operation of cleaning the second path 195, the first valve 113 included in the first channel 111 and the second valve 119 included in the second channel 117 may be turned off, that is, may be closed.

Figure 4A:
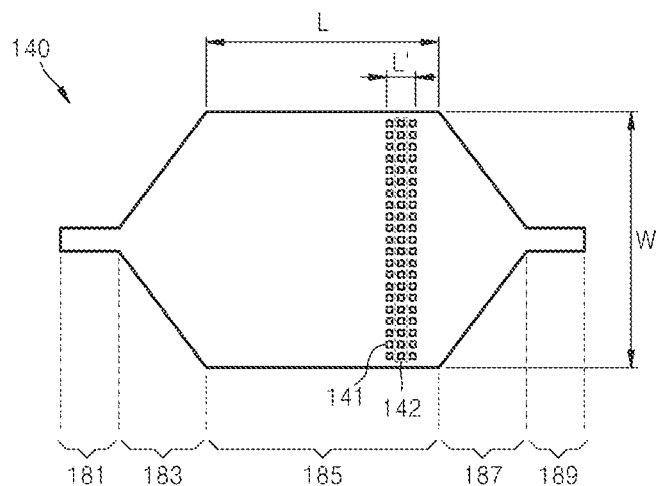
FIG. 4A is a schematic plan view of a filter portion included in the fluid controlling apparatus of FIG. 1, according to an embodiment of the present invention.
Figure 4B:
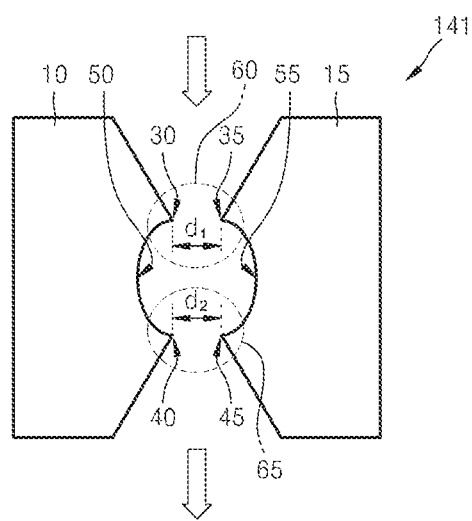
FIGS. 4B and 4C are schematic plan views of filter units included in a filter portion, according to an embodiment of the present invention.
Figure 4C:
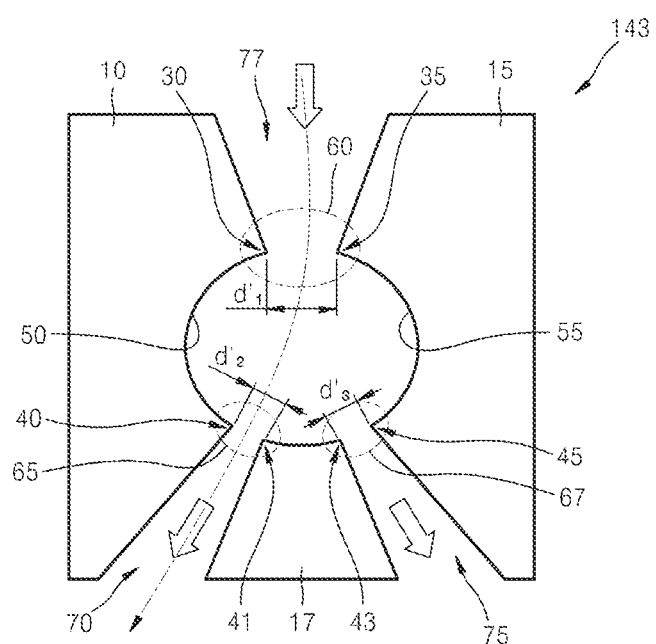
Figure 4D:
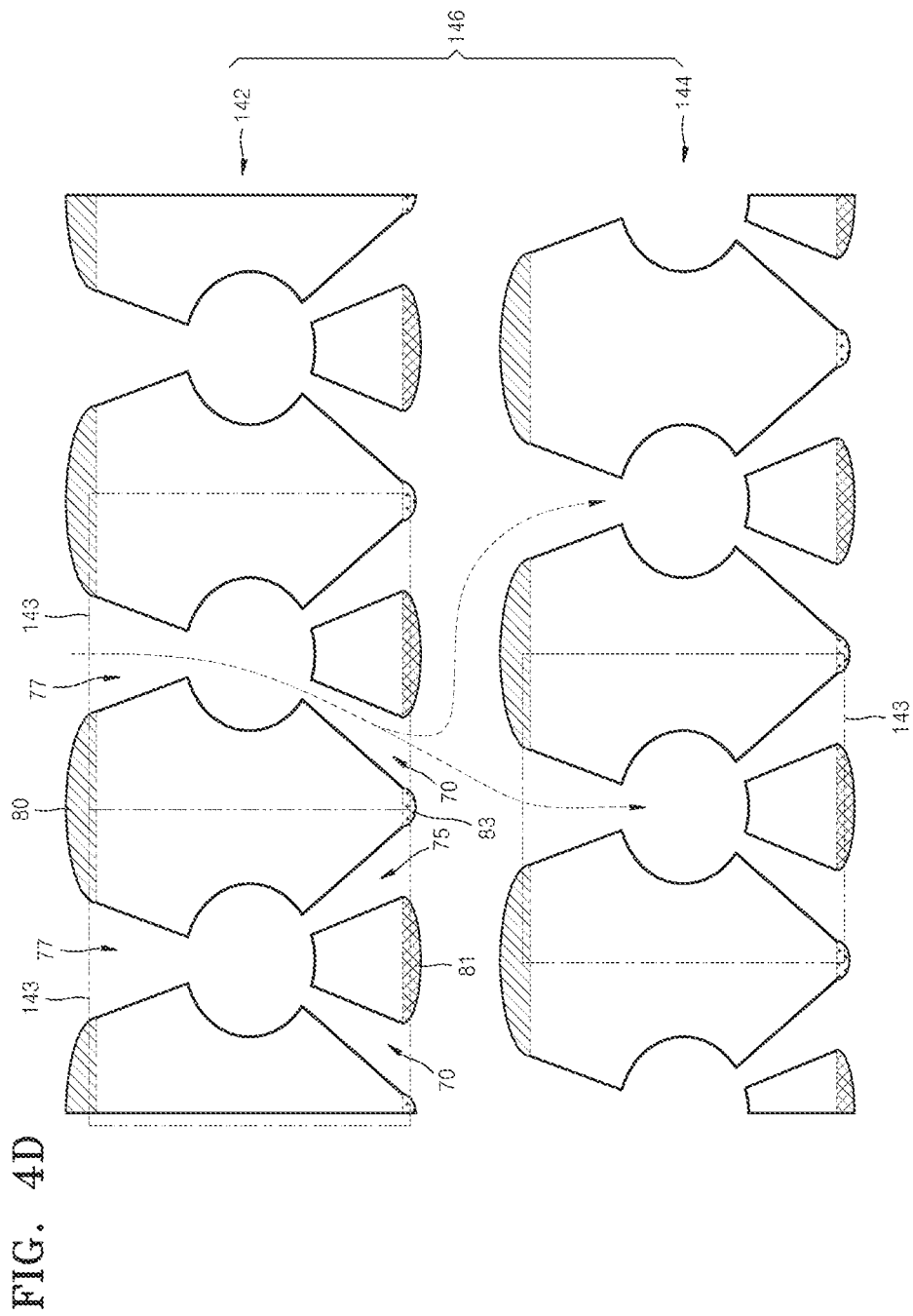
FIG. 4D is a schematic plan view of a filter sequence in which a plurality of filter units are arranged, according to an embodiment of the present invention.

Hereinafter, the filter portion 140 for filtering the target materials is described in detail. FIG. 4A is a schematic plan view of the filter portion 140 included in the fluid controlling apparatus 100 of FIG. 1, according to an embodiment of the present invention. FIGS. 4B and 4C are schematic plan views of filter units 141 and 143 included in the filter portion 140, according to an embodiment of the present invention. FIG. 4D is a schematic plan view of a filter sequence 146 in which a plurality of filter units 143 are arranged, according to an embodiment of the present invention.

Referring to FIG. 4A, the filter portion 140 may include an inlet 181 to which fluids are introduced, a filter region 185 in which a plurality of filter units 141 are arranged, and an outlet 189 for discharging fluids. In addition, a first connection portion 183 may be further disposed between the filter region 185 and the inlet 181. The first connection portion 183 may have a tapered shape and may widens toward the filter region 185 from the inlet 181.

The filter region 185 may include the filter units 141. The filter units 141 may constitute a plurality of filter sequences 142 that are arranged in parallel to each other. The target materials included in the fluid may be captured by the filter unit 141. A width W of the filter region 185 may be greater than a length L of the filter region 185. For example, a ratio of the width W to the length L of the filter region 185 may be 3:1 or greater. In addition, the ratio of the width W to the length L of the filter region 185 may be 3:1 or greater and 100:1 or smaller. In more detail, the ratio of the width W to the length L of the filter region 185 may be 3:1 or greater and 50:1 or smaller, for example, 3:1 or greater and 30:1 or smaller. When the width W of the filter region 185 is greater than the length L of the filter region 185, a maximum velocity of a fluid passing through the filter region 185 or a maximum pressure applied to the filter region 185 may be reduced.

A second connection portion 187 may further be disposed between the filter region 185 and the outlet 189. The second connection portion 187 may have a tapered shape and may narrow toward the outlet 189 from the filter region 185.

FIG. 4B shows the filter unit 141 included in the filter portion 140 of FIG. 4A. The filter unit 141 may include a first portion 10 and a second portion 15 that is spaced apart from the first portion 10 to face the first portion 10. The first portion 10 may include a plurality of protrusions, for example, first and second protrusions 30 and 40, protruding toward the second portion 15. The second portion 15 may include a plurality of protrusions, for example, third and fourth protrusions 35 and 45, protruding toward the first portion 10. The third and fourth protrusions 35 and 45 of the second portion 15 may be disposed to correspond to the first and second protrusions 30 and 40 of the first portion 10, respectively.

The plurality of protrusions of the first portion 10 may include the first protrusion 30 and the second protrusion 40, which are spaced apart from each other. The plurality of protrusions of the second portion 15 may include the third protrusion 35 and the fourth protrusion 45, which are spaced apart from each other. Here, the first protrusion 30 and the third protrusion 35 may be spaced apart to face each other, and a first distance $d_1$ between the first protrusion 30 and the third protrusion 35 may be adjusted according to the sizes of target materials to be filtered. The first distance $d_1$ between the first protrusion 30 and the third protrusion 35 may range from several μm to several hundred μm. For example, the first distance $d_1$ may range from about 1 μm to about 500 μm, and particularly, the first distance $d_1$ may range from about 5 μm to about 100 μm.

The second protrusion 40 and the fourth protrusion 45 may also be spaced apart to face each other. A second distance $d_2$ between the second protrusion 40 and the fourth protrusion 45 may be adjusted according to the sizes of target materials to be captured. The second distance $d_2$ between the second protrusion 40 and the fourth protrusion 45 may range from several μm to several hundred μm. For example, the second distance $d_2$ may range from about 1 μm to about 500 μm, and particularly, the second distance $d_2$ may range from about 5 μm to about 100 μm. The first distance $d_1$ between the first protrusion 30 and the third protrusion 35 may be greater than or equal to the second distance $d_2$ between the second protrusion 40 and the fourth protrusion 45. The size of the filter unit 141 may refer to the first distance $d_1$ between the first protrusion 30 and the third protrusion 35 or the second distance $d_2$ between the second protrusion 40 and the fourth protrusion 45.

The filter unit 141 may include a first capturing portion 60 and a second capturing portion 65. A fluid including target materials may be introduced in a direction indicated by an arrow on an upper side of FIG. 4B, and may be discharged in a direction indicated by an arrow on a lower side of FIG. 4B. The target materials may be captured by at least one of the first capturing portion 60 and the second capturing portion 65. Accordingly, since the filter unit 141 includes more structures capable of capturing target materials than a comparative filter having one capturing structure, target materials are more likely to be captured in the filter unit 141 than in the comparative filter.

The first capturing portion 60 may be formed by the first protrusion 30 and the third protrusion 35 and may capture target materials. The first protrusion 30 and the third protrusion 35 may be tapered toward ends thereof, so that the target materials may be easily filtered by the first capturing portion 60. That is, target materials included in a fluid may be supported by the first capturing portion 60 so as not to leak out of the filter unit 141 along with the fluid. Also, although the ends of the first protrusion 30 and the third protrusion 35 are sharp, the present embodiment is not limited thereto. That is, the ends of the first protrusion 30 and the third protrusion 35 may be blunt. In this case, while target materials pass between the blunt ends of the first protrusion 30 and the third protrusion 35, a moving speed of the target materials may be reduced due to a friction force.

The second capturing portion 65 may be formed by the second protrusion 40 and the fourth protrusion 45 and may also capture target materials. The second protrusion 40 and the fourth protrusion 45 may taper toward ends thereof, so that the target materials may be easily filtered by the second capturing portion 65. That is, target materials included in a fluid may be supported by the second capturing portion 65 so as not to leak out of the filter unit 141 along with the fluid. Also, the ends of the second protrusion 40 and the fourth protrusion 45 may be sharp. A space between the first protrusion 30 and the second protrusion 40 and a space between the third protrusion 35 and the fourth protrusion 45 may be defined by curved surfaces 50 and 55, respectively, extended between the respective pair of protrusions. Thus, spaces where captured materials exist are increased, and damage to target materials to be captured due to contact with the filter unit 141 may be reduced or effectively prevented.

When the second capturing portion 65 captures target materials, even when a fluid leaking out of the filter unit 141 flows backwards through the filter unit 141, the first protrusion 30 and the third protrusion 35 may support captured target materials. Accordingly, leaking out of the captured target materials from the filter unit 141 along with the fluid is reduced or effectively prevented. Also, if the second distance $d_2$ between the second protrusion 40 and the fourth protrusion 45 is less than the first distance $d_1$ between the first protrusion 30 and the third protrusion 35, target materials are more likely to be captured. Also, target materials of different sizes may be captured by the first and second capturing portions 60 and 65. The first capturing portion 60 formed by the first protrusion 30 and the third protrusion 35 and the second capturing portion 65 formed by the second protrusion 40 and the fourth protrusion 45 may be referred to as obstacle structures. Accordingly, the filter unit 141 may include multiple obstacle structures.

For example, since the filter unit 141 may capture CTCs respectively in the first capturing portion 60 and the second capturing portion 65, target materials are more likely to be captured. That is, since CTCs are surrounded by flexible cell membranes, the CTCs may be deformed to some extent. Undeformed CTCs may be captured by the first capturing portion 60, and deformed CTCs may be captured by the second capturing portion 65, thereby reducing the number of CTCs that are not filtered, that is, CTCs that are lost. Since the filter unit 141 may filter only desired target materials, the time taken to analyze target materials may be reduced. Also, since there is no need to re-separate the desired target materials from other molecules, efficiency and convenience may be improved.

FIG. 4C shows the filter unit 143, which may be included in the filter portion 140 of FIG. 4A. The filter unit 143 may include a first portion 10, a second portion 15 that is spaced apart from the first portion 10 to face the first portion 10, and a third portion 17 disposed between the first and second portions 10 and 15. An introduction channel 77 may be disposed between upper portions of the first and second portions 10 and 15. The third portion 17 may be disposed between lower portions of the first and second portions 10 and 15. A first discharge channel 70 may be formed between the first and third portions 10 and 17, and a second discharge channel 75 may be formed between the second and third portions 15 and 17. The filter unit 143 may form more discharge channels by being divided into more portions.

The first portion 10 may include a first protrusion 30 and a second protrusion 40, protruding toward the second portion 15. The second portion 15 may include a third protrusion 35 and a fourth protrusion 45, protruding toward the first portion 10. The third portion 17 may include a fifth protrusion 41 protruding in the second direction, that is, toward the portion 10, and a sixth protrusion 43 protruding in the first direction, that is, toward the second portion 15.

The first protrusion 30 may correspond to the third protrusion 35, and a first capturing portion 60 may be formed by the first protrusion 30 and the third protrusion 35. The second protrusion 40 may correspond to the fifth protrusion 41, and a second capturing portion 65 may be formed by the second protrusion 40 and the fifth protrusion 41. The fourth protrusion 45 may correspond to the sixth protrusion 43, and a third capturing portion 67 may be formed by the fourth protrusion 45 and the sixth protrusion 43.

The size of the first capturing portion 60, that is, a distance $d_1$ between the first and third protrusions 30 and 35, the size of the second capturing portion 65, that is, a distance $d_2$ between the second and fifth protrusions 40 and 41, or the size of the third capturing portion 67, that is, a distance $d_3$ between the fourth and sixth protrusions 45 and 43 may be adjusted according to the sizes of target materials to be filtered. The distances $d_1$, $d_2$, and $d_3$ may range from several μm to several hundred μm. For example, the distances $d_1$, $d_2$, and $d_3$ may range from about 1 μm to about 500 μm, and particularly, range from about 5 μm to about 100 μm.

Since the filter unit 143 may include a plurality of capturing portions, for example, the first capturing portion 60, the second capturing portion 65, and the third capturing portion 67, target materials are more likely to be captured in the filter unit 143. A fluid including target materials may be introduced in a direction indicated by an arrow of FIG. 4C, and may be discharged via the first discharge channel 70 shown in a lower side of FIG. 4C. In other words, the first discharge channel 70 connected to the second capturing portion 65 or the second discharge channel 75 connected to the third capturing portion 67 may serve as a discharge path of a fluid. For example, when the third capturing portion 67 captures a target material, although the target material blocks the second discharge channel 75, the fluid may be discharged to the first discharge channel 70 connected to the second capturing portion 65 that does not capture the target material. Further, molecules, other than the target material, along with the fluid may be discharged to the first discharge channel 70. Thus, the pressure inside the filter unit 143 is kept low, and application of a high pressure to the target material and losing of the target material from the filter unit 143 may be reduced or effectively prevented.

Referring to FIG. 4D, the filter portion 140 of FIG. 4A may include a plurality of filter sequences 146 arranged in parallel to each other in a direction from the inlet 181 towards the outlet 189. Each of the filter sequences 146 may include a plurality of filter units 143. The plurality of filter units 143 may be spaced apart from each other or be adjoined with each other and be aligned with each other. Alternatively, each of the filter sequences 146 may include a plurality of filter units 141.

The plurality of filter sequences 146 may include an $n^{th}$ (n is a natural number) filter sequence 142 and an $(n+1)^{th}$ filter sequence 144 arranged in parallel to each other in the direction from the inlet 181 to the outlet 189. Filter unit 143 included in the $n^{th}$ filter sequence 142 and a filter unit 143 included in the $(n+1)^{th}$ filter sequence 144 may not be disposed in line. That is, filter units included in the $n^{th}$ filter sequence 142 and filter units included in the $(n+1)^{th}$ filter sequence 144 may be disposed in a zigzag manner. Thus, if the $n^{th}$ filter sequence 142 and the $(n+1)^{th}$ filter sequence 144 are disposed in zigzags, a fluid, target materials included in the fluid, and other molecules may have various movement paths. Alternatively, the filter units included in the $n^{th}$ filter sequence 142 and the filter units included in the $(n+1)^{th}$ filter sequence 144 may not be disposed in zigzags and may be disposed parallel to each other.

First, second, and third convex portions 80, 81, and 83 may be further disposed on front surfaces of the $n^{th}$ and $(n+1)^{th}$ filter sequences 142 and 144 through which the fluid is introduced and on rear surfaces thereof through which the fluid is discharged. The first, second, and third convex portions 80, 81, and 83 may protrude from the front surfaces and the rear surfaces and be referred to as stagnation prevention portions that prevent a stagnation of the fluid. The first convex portion 80 may be disposed between introduction channels 77 of adjacent filter units 143. The second convex portion 81 may be disposed between first and second discharge channels 70 and 75. The third convex portion 83 may be disposed between the second discharge channel 75 of the filter unit 143 and a first discharge channel 70 of adjacent filter unit 143. The first, second, and third convex portions 80, 81, and 83 may reduce or effectively prevent accumulation of target materials or other molecules due to a stagnant fluid around the $n^{th}$ filter sequence 142 and the $(n+1)^{th}$ filter sequence 144.

Figure 5:
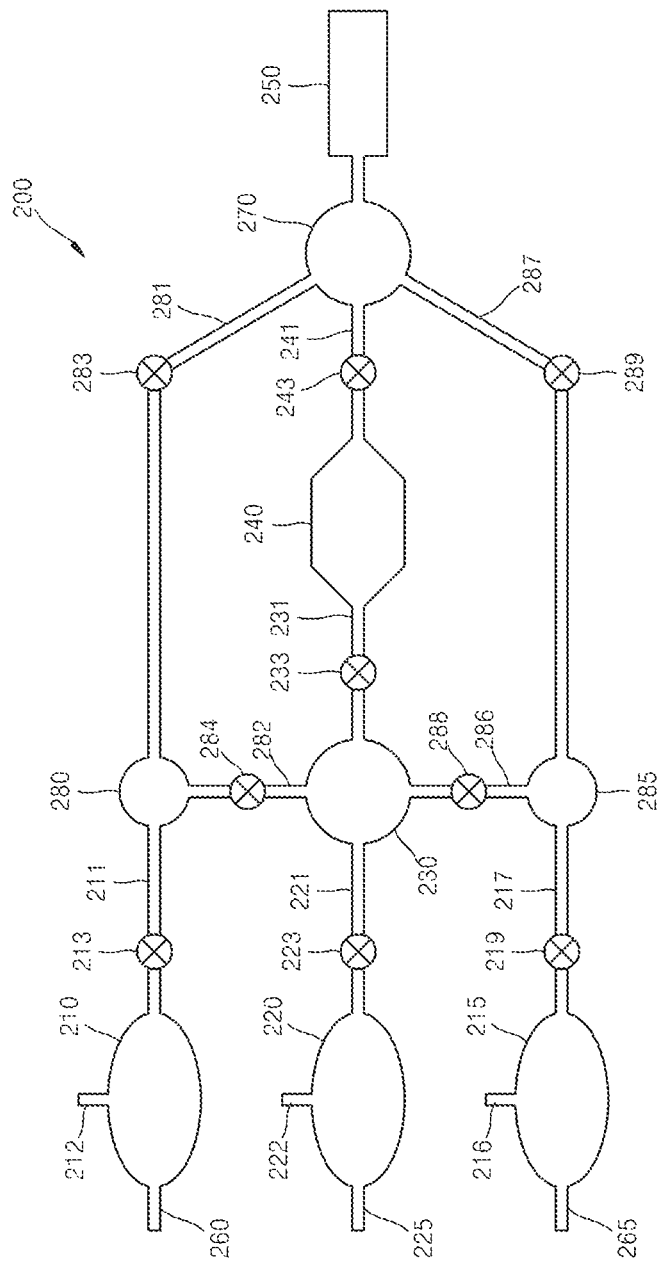
FIG. 5 is a schematic structural diagram of a fluid controlling apparatus according to another embodiment of the present invention.

FIG. 5 is a schematic structural diagram of a fluid controlling apparatus 200 according to another embodiment of the present invention.

Referring to FIG. 5, the fluid controlling apparatus 200 may include at least one sample chamber, a cleaning chamber 220, a first multi-port 230 connected to the at least one sample chamber and the cleaning chamber 220, a filter portion 240 that is connected to the first multi-port 230 and filters the target materials, a second multi-port 270 connected to the filter portion 240, and a first pump 250 connected to the second multi-port 270. In addition, the fluid controlling apparatus 200 may further include at least one 3-way port for connecting the at least one sample chamber, the first multi-port 230, and the second multi-port 270 to each other.

The at least one sample chamber may include first and second sample chambers 210 and 215, respectively. A fluid including the target materials may be introduced to each of the first and second sample chambers 210 and 215. The fluid may be introduced to the first and second sample chambers 210 and 215 through first and second inlets 212 and 216 that are included in the first and second sample chambers 210 and 215, respectively, from an external source. FIG. 5 shows a case where two sample chambers, that is, the first and second sample chambers 210 and 215 are used. However, the number of sample chambers may differ.

A cleaning solution may be introduced to the cleaning chamber 220 and may clean components of the fluid controlling apparatus 200. The cleaning solution may be introduced to the cleaning chamber 220 through a third inlet 222 included in the cleaning chamber 220. FIG. 5 shows a case where a single cleaning chamber, that is, the cleaning chamber 220, is used. However, the number of cleaning chambers may differ.

The first multi-port 230 may be connected to the first and second sample chambers 210 and 215 through 3-way ports 280 and 285, respectively. That is, the first and second sample chambers 210 and 215 may be connected to the 3-way ports 280 and 285 through first and second channels 211 and 217, respectively. The 3-way ports 280 and 285 may be connected to the first multi-port 230 through sixth and eighth channels 282 and 286, respectively. The 3-way ports 280 and 285 may be connected to the second multi-port 270 through fifth and seventh channels 281 and 287, respectively. The first multi-port 230 may be connected to the cleaning chamber 220 through a third channel 221.

First through third valves 213, 219, and 223 for opening and closing channels may be included in the first through third channels 211, 217, and 221, respectively. That is, the first through third valves 213, 219, and 223 may control flow of fluids that flow through the first through third channels 211, 217, and 221, respectively. In addition, fifth through eighth valves 283, 284, 289, and 288 for opening and closing channels may be included in fifth through eighth channels 281, 282, 287, and 286. That is, the fifth through eighth valves 283, 284, 289, and 288 may control flow of fluids that flow through the fifth through eighth channels 281, 282, 287, and 286, respectively.

For example, when the first valve 213 included in the first channel 211 is turned on, the fluid or the cleaning solution may flow between the first sample chamber 210 and the 3-way port 280 through the first channel 211. On the other hand, for example, when the third valve 223 included in the third channel 221 is turned off, the fluid or the cleaning solution may not flow between the cleaning chamber 220 and the first multi-port 230 through the third channel 221. If the fluid controlling apparatus 200 further includes another sample chamber or another cleaning chamber, the fluid controlling apparatus 200 may further include more 3-way ports and more channels may be connected to the first and second multi-ports 230 and 270.

The filter portion 240 may filter the target materials included in the fluid. The filter portion 240 may include a plurality of filter units that have been described already. The filter portion 240 may be connected to the first multi-port 230 through a fourth channel 231. The fourth channel 231 may further include a fourth valve 233 for opening and closing the fourth channel 231 and controlling flow of fluids that flow through the fourth channel 231.

The second multi-port 270 may be connected to the filter portion 240 through a ninth channel 241. As described above, the second multi-port 270 may be connected to the 3-way ports 280 and 285 through the fifth and seventh channels 281 and 287, respectively.

The first pump 250 may be connected to the second multi-port 270. The first pump 250 applies a pressure to the fluid controlling apparatus 200, so that the fluid including the target materials and the cleaning solution may flow in the fluid controlling apparatus 200. The first pump 250 may apply a negative pressure to the fluid controlling apparatus 200 and may be, for example, a vacuum pump. In this case, first through third air vents 260, 265, and 225 may be formed in the first and second sample chambers 210 and 215 and the cleaning chamber 220, respectively. Thus, when the first pump 250 applies a negative pressure to the fluid controlling apparatus 200, air may be introduced from the first through third air vents 260, 265, and 225, and the fluid and the cleaning solution may flow in a direction from the first and second sample chambers 210 and 215 and the cleaning chamber 220 toward the first pump 250.

A method of controlling a fluid by using the fluid controlling apparatus 200 of FIG. 5 will now be described. The method may include passing the fluid including the target materials and the cleaning solution from the at least one sample chamber to the filter portion 240 and cleaning a path through which the fluid passes by flowing the cleaning solution through the path.

Figure 6:
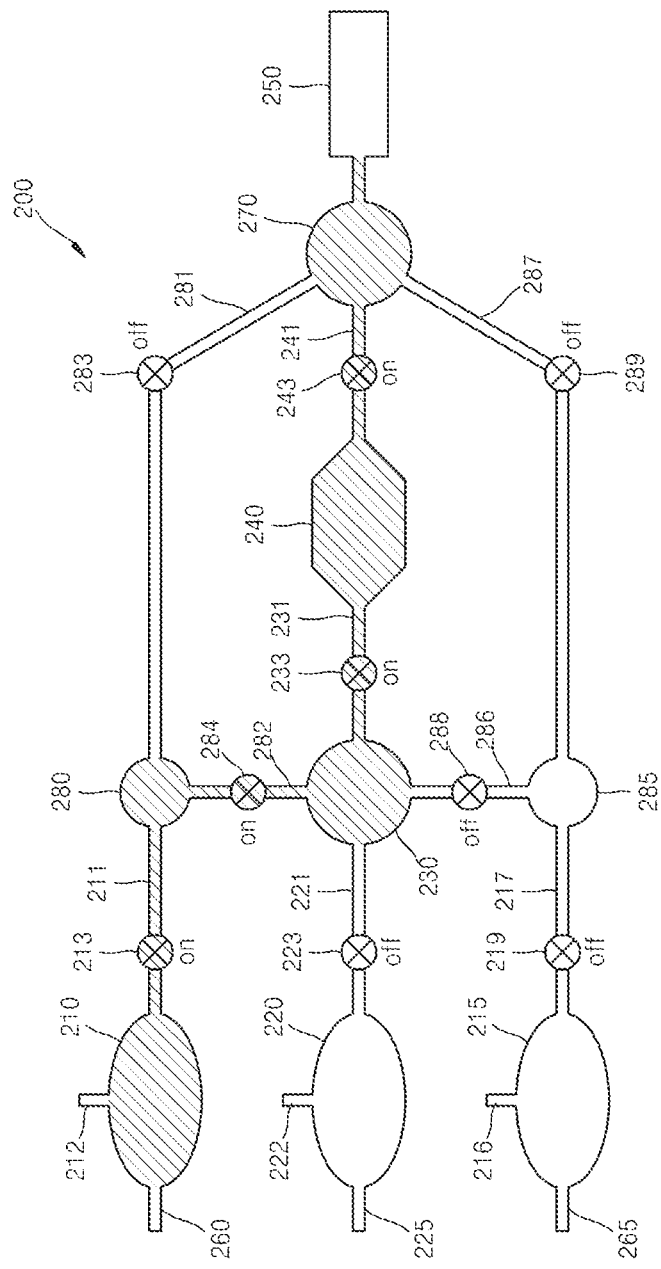
FIG. 6 is a structural diagram for describing a method of controlling a fluid by using a fluid controlling apparatus, according to another embodiment of the present invention.

FIG. 6 is a structural diagram for describing an operation of passing the fluid, including the target materials, from the at least one sample chamber to the filter portion 240 in the method of controlling a fluid, according to another embodiment of the present invention.

Referring to FIG. 6, the fluid including the target materials may be introduced to the first sample chamber 210 through the first inlet 212. The fluid may flow in a direction from the first sample chamber 210 toward the first pump 250 by a negative pressure applied by the first pump 250. That is, the fluid may flow from the first sample chamber 210 to the filter portion 240 through the 3-way port 280 and the first multi-port 230.

In more detail, the fluid may reach the 3-way port 280 from the first sample chamber 210 through the first channel 211. In addition, the first valve 213 for opening and closing the first channel 211 may be turned on, that is, may be opened. Then, the fluid may flow from the 3-way port 280 to the first multi-port 230 through the sixth channel 282. In this case, the sixth valve 284 for opening and closing the sixth channel 282 may be turned on, that is, may be opened. In addition, the fluid may flow from the first multi-port 230 to the filter portion 240 through the fourth channel 231. In this case, the fourth valve 233 for opening and closing the fourth channel 231 may be turned on, that is, may be opened. While the fluid passes through the filter portion 240, the target materials may be filtered and the remaining fluid may be discharged out of the fluid controlling apparatus 200 through the second multi-port 270. The filter portion 240 may be connected to the second multi-port 270 through the ninth channel 241. In this case, a ninth valve 243 for opening and closing the ninth channel 241 may be turned on, that is, may be opened.

In the operation of passing the fluid in the filter portion 240, the third valve 223 included in the third channel 221 may be turned off, that is, may be closed. In addition, the fifth, seventh, and eighth valves 283, 289, and 288 that are included in the fifth, seventh, and eighth channels 281, 287, and 286, respectively, may be turned off, that is, may be closed.

Figure 7A:
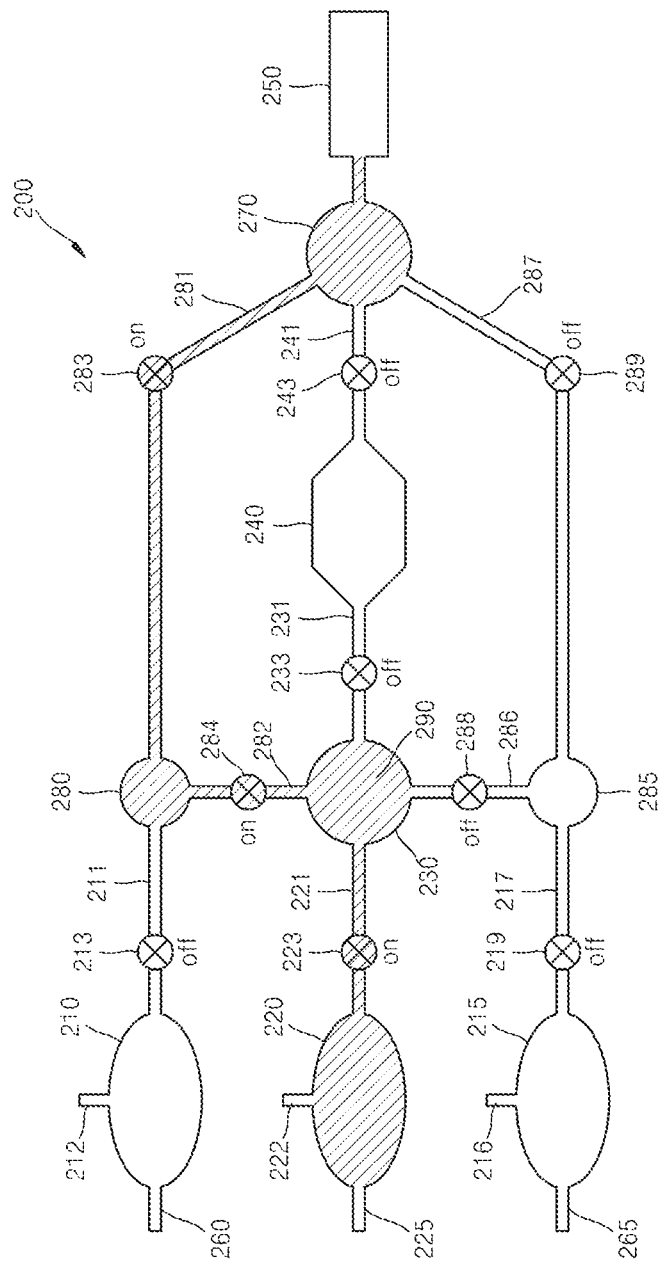

FIGS. 7A and 7B are structural diagrams for describing operations of cleaning paths through which fluids pass in the method of controlling a fluid, according to another embodiment of the present invention.

FIG. 7A shows an operation of cleaning a third path 290. The cleaning solution may be introduced to the cleaning chamber 220 through the third inlet 222. The cleaning solution may flow in a direction from the cleaning chamber 220 towards the first pump 250 by a negative pressure applied by the first pump 250. The cleaning solution may be discharged out of the fluid controlling apparatus 200 from the cleaning chamber 220 through the first multi-port 230, the 3-way port 280, the second multi-port 270.

In more detail, the cleaning solution may flow from the cleaning chamber 220 to the first multi-port 230 through the third channel 221. In this case, the third valve 223 for opening and closing the third channel 221 may be turned on, that is, may be opened. Then, the cleaning solution may reach the 3-way port 280 from the first multi-port 230 through the sixth channel 282. In this case, the sixth valve 284 for opening and closing the sixth channel 282 may be turned on, that is, may be opened. In addition, the cleaning solution may reach the second multi-port 270 from the 3-way port 280 through the fifth channel 281. In this case, the fifth valve 283 for opening and closing the fifth channel 281 may be turned on, that is, may be opened.

The cleaning solution may remove the fluid that remains on the third path 290 and pollutants included in the fluid while passing the third path 290. Thus, the fluid controlling apparatus 200 may prevent components of the fluid controlling apparatus 200 from being contaminated by the pollutants and the path through which the fluid passes from clogging due to the pollutants. The cleaning solution may be discharged out of the fluid controlling apparatus 200 from the second multi-port 270. In the operation of cleaning the third path 290, the first valve 213 included in the first channel 211 and the fourth valve 233 included in the fourth channel 231 may be turned off, that is, may be closed. In addition, the eighth and ninth valves 288 and 243 included in the eighth and ninth channels 286 and 241 may also be turned off, that is, may be closed. Also, the second and seventh valves 219 and 289 included in the second and seventh channels 217 and 287 may also be turned off, that is, may be closed.

FIG. 7B shows an operation of cleaning a fourth path 295, according to another embodiment of the present invention. The cleaning solution may be introduced to the cleaning chamber 220 through the third inlet 222. The cleaning solution may flow in a direction from the cleaning chamber 220 towards the first pump 250 by a negative pressure applied by the first pump 250. That is, the cleaning solution may be discharged out of the fluid controlling apparatus 200 from the cleaning chamber 220 through the first multi-port 230, the filter portion 240, and the second multi-port 270.

In more detail, the cleaning solution may flow from the cleaning chamber 220 to the first multi-port 230 through the third channel 221. In this case, the third valve 223 for opening and closing the third channel 221 may be turned on, that is, may be opened. Then, the cleaning solution may reach the filter portion 240 from the first multi-port 230 through the fourth channel 231. In this case, the fourth valve 233 for opening and closing the fourth channel 231 may be turned on, that is, may be opened. The cleaning solution may reach the second multi-port 270 from the filter portion 240 through the ninth channel 241. In this case, the ninth valve 241 for opening and closing the ninth channel 241 may be turned on, that is, may be opened.

The cleaning solution may remove the fluid that remains on the fourth path 295 and pollutants included in the fluid while passing through the fourth path 295. Thus, the fluid controlling apparatus 200 may prevent components of the fluid controlling apparatus 200 from being contaminated by the pollutants and the path through which the fluid passes from clogging due to the pollutants. Lastly, the cleaning solution may be discharged out of the fluid controlling apparatus 200 from the second multi-port 270.

In the operation of cleaning the fourth path 295, the fifth through eighth valves 283, 284, 289, and 288 that are respectively included in the fifth through eighth channels 281, 282, 287, and 286 may be turned off, that is, may be closed. In addition, the first and second valves 213 and 219 that are respectively included in the first and second channels 211 and 217 may be turned off, that is, may be closed.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A fluid controlling apparatus comprising:
   at least one sample chamber for holding a fluid containing target materials;
   a cleaning chamber for holding a cleaning solution;
   a first multi-port connected to the at least one sample chamber through a first channel and connected to the cleaning chamber through a second channel;
   a filter portion, connected to the first multi-port through a third channel, for filtering the target materials;
   a first pump, connected to the filter portion, for applying pressure
   a first air vent connected to the at least one sample chamber;
   a second air vent connected to the cleaning chamber;
   a valve for opening and closing the second air vent connected to the cleaning chamber; and
   a second pump, connected to the cleaning chamber, for applying pressure.

2. The fluid controlling apparatus of claim 1, further comprising:
   a valve for opening and closing the first channel;
   a valve for opening and closing the second channel; and
   a valve for opening and closing the third channel.

3. The fluid controlling apparatus of claim 1, further comprising a second multi-port connected to the filter portion and the first pump.

4. The fluid controlling apparatus of claim 3, further comprising at least one 3-way port connecting the at least one sample chamber and the first and second multi-ports.

5. The fluid controlling apparatus of claim 1, wherein the filter portion comprises a plurality of filter sequences and the plurality of filter sequences comprises a plurality of filter units.

6. The fluid controlling apparatus of claim 5, wherein each of the plurality of filter units comprises:
   a first portion comprising a first plurality of protrusions protruding in a first direction; and
   a second portion spaced apart from the first portion and facing the first portion, the second portion comprising a second plurality of protrusions protruding toward the first portion and corresponding to the first plurality of protrusions.

7. The fluid controlling apparatus of claim 6, wherein each of the plurality of filter units further comprises:
   a third portion disposed between the first portion and the second portion;
   a first fluid discharge channel located between the first portion and third portion; and
   a second fluid discharge channel located between the second portion and the third portion.

8. A method of controlling fluid using the fluid controlling apparatus of claim 1, the method comprising:
   passing the fluid containing target materials from the at least one sample chamber to the filter portion; and
   cleaning a path of the fluid by passing the cleaning solution through the path.

9. The method of claim 8, wherein passing the fluid to the filter portion comprises passing the fluid held by the at least one sample chamber from the at least one sample chamber to the filter portion through the first multi-port as pressure is applied by the first pump.

10. The method of claim 9, wherein passing the fluid to the filter portion comprises:
    opening a valve for opening and closing the first channel;
    opening a valve for opening and closing the third channel; and
    closing a valve for opening and closing the second channel.

11. The method of claim 8, wherein cleaning the path of the fluid comprises:
    cleaning a first path from the cleaning chamber to the at least one sample chamber through the first multi-port; and
    cleaning a second path from the cleaning chamber to the filter portion through the first multi-port.

12. The method of claim 11, wherein cleaning the first path comprises:
    opening a valve for opening and closing the first channel;
    opening a valve for opening and closing the second channel;
    closing a valve for opening and closing the third channel;
    closing a valve for opening and closing an air vent connected to the cleaning chamber; and
    applying pressure to the cleaning chamber.

13. The method of claim 12, wherein a second pump connected to the cleaning chamber applies the pressure to the cleaning chamber.

14. The method of claim 11, wherein cleaning the second path comprises:
    closing a valve for opening and closing the first channel;
    opening a valve for opening and closing the second channel;
    opening a valve for opening and closing the third channel; and
    applying pressure to the fluid controlling apparatus.

15. The method of claim 14, wherein the first pump applies pressure to the fluid controlling apparatus.

16. The method of claim 8, wherein the fluid controlling apparatus comprises:
    a second multi-port connected to the filter portion and the first pump; and at least one 3-way port connecting the at least one sample chamber and the first and second multi-ports, wherein passing the fluid to the filter portion comprises passing the fluid held by the at least one sample chamber from the at least one sample chamber to the filter portion and the second multi-port through the at least one 3-way port and the first multi-port as pressure is applied by the first pump.

17. The method of claim 16, wherein passing the fluid to the filter portion comprises:

closing a valve for opening and closing the second channel; and closing a valve for opening and closing a fifth channel connecting the at least one 3-way port and the second multi-port.

18. The method of claim 16, wherein cleaning the path comprises:

cleaning a third path from the cleaning chamber to the second multi-port through the first multi-port and the at least one 3-way port; and cleaning a fourth path from the cleaning chamber to the filter portion and the second multi-port through the cleaning chamber and the first multi-port.

19. The method of claim 18, wherein cleaning the third path comprises:

closing a valve for opening and closing the first channel; and closing a valve for opening and closing the third channel.

20. The method of claim 18, wherein cleaning the fourth path comprises:

closing a valve for opening and closing a fifth channel connecting the at least one 3-way port and the second multi-port; and closing a valve for opening and closing a sixth channel connecting the at least one 3-way port and the first multi-port.

* * * * *